United States Patent
Hua et al.

(10) Patent No.: US 12,059,440 B2
(45) Date of Patent: *Aug. 13, 2024

(54) PREPARATION AND APPLICATION OF GRAIN WORM FOR TREATING DIABETES

(71) Applicants: Xiangrong Hua, Suzhou (CN); Amy Y. Huang, Pinecrest, FL (US)

(72) Inventors: Xiangrong Hua, Suzhou (CN); Amy Y. Huang, Pinecrest, FL (US)

(*) Notice: Subject to any disclaimer, the term of this patent is extended or adjusted under 35 U.S.C. 154(b) by 171 days.

This patent is subject to a terminal disclaimer.

(21) Appl. No.: 17/409,063

(22) Filed: Aug. 23, 2021

(65) Prior Publication Data

US 2022/0008484 A1 Jan. 13, 2022

Related U.S. Application Data

(63) Continuation of application No. 17/077,657, filed on Oct. 22, 2020, now Pat. No. 11,096,970, which is a continuation of application No. PCT/CN2019/104316, filed on Sep. 4, 2019.

(51) Int. Cl.
*A61K 35/64* (2015.01)
*A61P 3/08* (2006.01)
*A61K 9/00* (2006.01)
*A61K 9/19* (2006.01)

(52) U.S. Cl.
CPC .............. *A61K 35/64* (2013.01); *A61P 3/08* (2018.01); *A61K 9/0019* (2013.01); *A61K 9/19* (2013.01)

(58) Field of Classification Search
CPC ..................................................... A61K 35/64
See application file for complete search history.

(56) References Cited

U.S. PATENT DOCUMENTS 11,096,970 B2 8/2021 Hua et al.

FOREIGN PATENT DOCUMENTS

| | | |
|---|---|---|
| CN | 101103995 | 1/2008 |
| CN | 102335241 | 10/2012 |
| CN | 103251100 | 8/2013 |
| CN | 104174009 | 12/2014 |
| CN | 108404088 | 8/2018 |
| CN | 110327373 | 10/2019 |
| KR | 101668949 | 10/2014 |

(Continued)

OTHER PUBLICATIONS

English machine translation of Yoon et al., KR 101651908 B1, 2016.*

(Continued)

*Primary Examiner* — Rosanne Kosson
(74) *Attorney, Agent, or Firm* — Malloy & Malloy, PL

(57) ABSTRACT

This invention discloses the preparation and the application of Grain Worm for treating diabetes or regulating blood insulin level. The Grain Worm can be in the form of dry powder, tincture, or extracts by itself or in a compound. Grain Worm regulates the blood insulin levels and the human blood glucose level for treating diabetes. It has been discovered that Grain Worm can effectively treat diabetes in humans through reducing insulin resistance and improving the β-cell function. The effect of this agent can last a long period of time (2-5 years). This is the first major discovery of using Grain Worm in treating diabetes.

16 Claims, 2 Drawing Sheets

(56) References Cited

FOREIGN PATENT DOCUMENTS

WO     WO2012134005     10/2012
WO     WO2021007933     1/2021

OTHER PUBLICATIONS

Guo et al., English language translation of Guo et al. CN 102335241 A, Feb. 1, 2012.
Marineau et al., Maggot debridement therapy in the treatment of complex diabetic wounds, Hawai'i Med J 70 121-124, 2011.
Qin, Ronggui et al, (Chinese Journal of Public Health), Hypoglycemic effect of housefly maggot chitosan in diabetic mice. vol. 26, No. 4, pp. 456-457, Apr. 30, 2010.

\* cited by examiner

PREPARATION AND APPLICATION OF GRAIN WORM FOR TREATING DIABETES

CLAIM OF PRIORITY

The present application is a continuation patent application of previously filed, now pending application having Ser. No. 17/077,657 filed on Oct. 22, 2020, which is set to mature into U.S. Pat. No. 11,096,970 on Aug. 24, 2021, which is a continuation patent application which claims the benefit of, pursuant to 35 U.S.C. Sections 120, 363, and 365(c), to a currently pending and prior filed international patent application, namely, that having Serial No. PCT/CN2019/104316 filed on Sep. 4, 2019. The aforementioned international patent application claims priority to a prior Chinese national patent application, namely, that having Serial No. 201910642595.3 filed on Jul. 16, 2019, the contents of which are both incorporated herein, by reference, in their entireties.

BACKGROUND OF THE INVENTION

Field of the Invention

The present invention provides a method for preparation of Grain Worm and a method for treating diabetes.

Description of the Related Art

Diabetes is a group of metabolic disorders characterized by high blood glucose (hyperglycemia) in patients. Hyperglycemia and particularly the type 2 diabetes mellitus (T2DM) are manifested by both insulin resistance and pancreatic β-cell dysfunction[1]. The prolonged hyperglycemia causes chronic damage and dysfunction of various tissues, especially on the eyes, kidneys, cardiovascular systems, and nerves. As discovered by modern science, the regulation of human blood glucose is a complex mechanism involving the secretion and the action of insulin, which is in turn regulated by other signals like glucagon, incretin peptide, growth factor, neurotransmitters, neuropeptides, and many others[2]. Due to this complexity, it is difficulty to attribute a single cause for the onset of T2DM. The existing method for treating T2DM usually starts with lifestyle change followed by the treatment with chemically synthesized medicine. As the T2DM progresses, the patients may eventually rely on exogenous insulin to control the blood glucose level. The existing method and medicine for treating diabetes are not satisfactory. Therefore, there are needs for new agents and methods with improved efficacy to treat diabetes in humans. This invention addresses these needs.

SUMMARY OF THE INVENTION

The present invention is related to the preparation of a naturally available agent (Grain Worm) and its applications in treating diabetes, through reducing insulin resistance, regulating blood glucose and insulin levels. The invention provides a method for the preparation of Grain Worm and its compounds for the application of treating diabetes. Moreover, the invention provides a method for treating diabetes with the Grain Worm and its compounds.

The method encompasses the regulation of blood insulin level with the Grain Worm and its compounds. This invention encompasses the Grain Worm and Grain Worm-based compounds used in any of medicine, dietary supplement, and food for regulating blood glucose and insulin levels. This invention encompasses the Grain Worm and the Grain Worm-based compounds in the form of dry powder, tincture, or extract.

The features of this invention include an agent that is a natural product with minimal toxicity that is easy to use. The agent can regulate blood glucose and insulin levels. The agent and method can effectively reduce insulin resistance and improve pancreatic β-cell function.

Other features and advantages of the present invention will become more apparent by reading the detailed description of the necessary embodiments with reference to FIG. 1 and FIG. 2.

DETAILED DESCRIPTION OF THE PREFERRED EMBODIMENT

Figure 1:
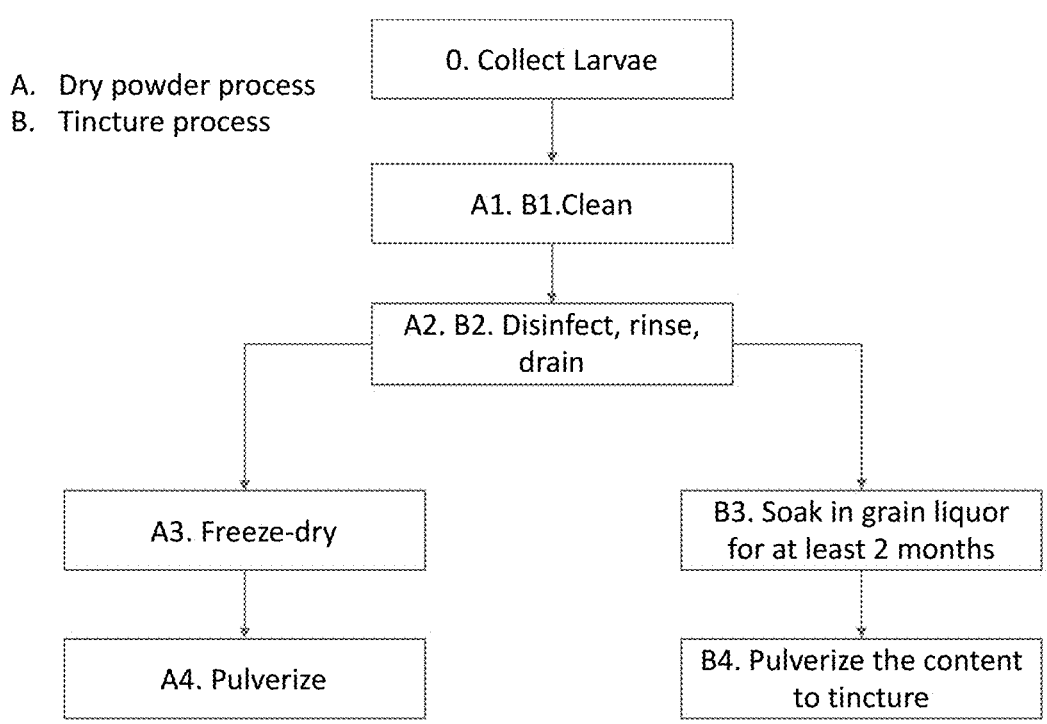
FIG. 1 is a flowchart illustrating the steps to prepare Grain Worm products.
Figure 2:
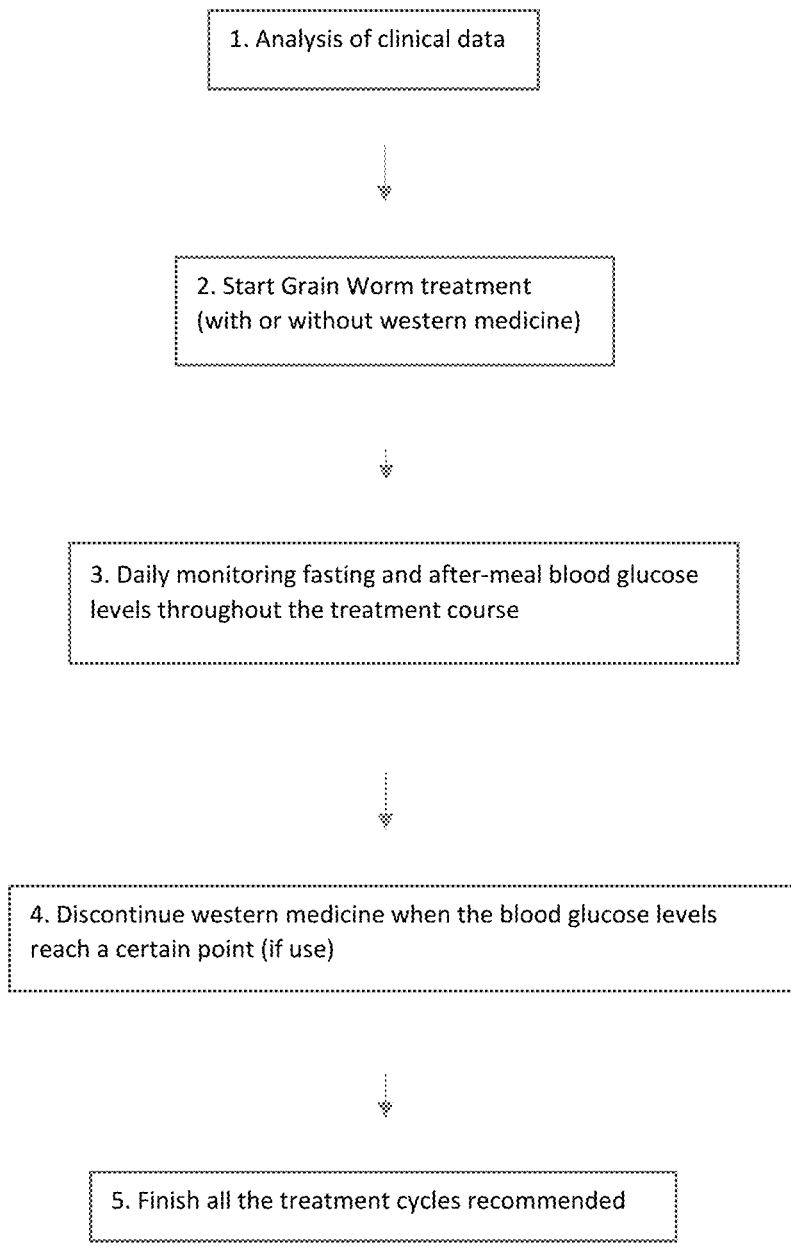
FIG. 2 is a flowchart illustrating the steps to use Grain Worm to treat diabetes.

The invention is described in detail below with reference to specific embodiments. The examples presented in this document will help those who are skilled in the field to further understand the present invention, but do not limit the invention in any form. It should be noted that, for those with basic skill in the field, several variations and improvements can be made without departing from the concept of this invention. These all belong to the protection scope of this invention.

Grain Worm is the name used in "Compendium of Materia Medica" (An ancient bible for traditional Chinese medicine), referring to the Larvae from a family of flies, particularly the *Chrysomyis megacephala* and *Lucilia sericata* families. It's commonly called maggot. The larvae contains protein, lysozyme, amino acids, and others. The Grain Worm is used in the compound in the form of dry powder, tincture, or extract.

Preparation of Grain Worm for Treating Diabetes

The method for preparing the Grain Worm dry powder includes the following steps:
- A1. Wash and scour the collected whole Grain Worm to remove the dirt on the surface;
- A2. Soak and disinfect the Grain Worm treated in Step A1, then rinse and drain;
- A3. Lyophilize drained Grain Worm into a freeze dryer until it dries to a water content of less than 10% by weight;
- A4. The freeze-dried whole larvae are pulverized at low temperature to obtain the dried Grain Worm powder.

The method for preparing the Grain Worm tincture includes the following steps:
- B1. Wash and scour the collected Grain Worm (Larvae) to remove the dirt on the surface;
- B2. Soak and disinfect the Grain Worm treated in step B1, then rinse and drain;
- B3. Store the drained whole Grain Worm into the liquor and seal it for a period of time;
- B4. Take out the sealed Grain Worm and pulverize it at low temperature to obtain the tincture.

The Grain Worm product can be in the form of capsule, tablet, pill, powder, compound granule, tincture, liquid agent, or a lyophilized powder. The Grain Worm extract includes any water-soluble extract, chemical soluble extract from whole Grain Worm or Grain Worm dry powder, and/or their combinations.

Method for Treating Diabetes

The invention also provides a method for treating diabetes based on the aforementioned compound, including the following steps:

Depending on the severity of diabetes (determined by the clinical test data), a treatment course of 1-6 cycles is recommended. Each cycle is three months. For each cycle, taking Grain Worm or a compound containing Grain Worm 2-3 times daily. The dosage of Grain Worm is 2 g-30 g per day. The invention also provides a method regulating insulin levels based on the aforementioned compound, including the following steps:

Depending on the severity of diabetes (determined by the clinical test data), a treatment course of 1-6 cycle is recommended. Each cycle is three months. For each cycle, taking Grain Worm or a compound containing Grain Worm 2-3 times daily. The dosage of Grain Worm is 2 g-30 g per day.

For the patients with pre-diabetes, taking Grain Worm or the compound containing Grain Worm for a period of 1-2 cycles. The dosage of Grain Worm is 2 g-15 g per day.

For the patients with confirmed diabetes, taking Grain Worm or the compound containing Grain Worm for a period of 4-6 cycles. The dosage of Grain Worm is 3 g-30 g per day for the first and second cycles; the dosage of Grain Worm is 3 g-15 g per day for the second cycle to sixth cycle.

Compared to the existing technology, the Grain Worm is a natural product with minimal toxicity. The active ingredient for treating diabetes is the whole Grain Worm. Modern medical research proves that the Grain Worm contains protein, fat, chitosan, antibacterial peptides and various amino acids. The lyophilized Grain Worm powder of this invention includes all the active ingredients of the whole Grain Worm, and the Grain Worm extract is mainly composed of fatty acids and/or proteins, peptides, amino acids, and the like. It was discovered that Grain Worm can regulate blood glucose and insulin levels. In the verification of the effect, it was found that the patients who were treated with Grain Worm could significantly reduce insulin resistance and improve β-cell functions. The Grain Worm does not have the drug resistance, the toxicity, and side effects of hypoglycemia, nephrotoxicity and hepatic toxicity.

Based on the results of Oral Glucose Tolerance Test (OGTT) before and after treatment with Grain Worm, the patients have their insulin resistance reduced and β-cell function improved, thus the blood glucose is controlled. The long-term effect after discontinuation of all medications has been observed. This is the first major discovery of using traditional Chinese medicine in treating diabetes.

This invention converts Grain Worm into a medicine, is convenient to carry and take, and has a high clinical effectiveness (up to 90% for a certain group of patients, based on existing statistics). The patients are followed up to five years after the treatment.

Grain Worm formulated compound, on the other hand, is an all-natural product that can effectively treat diabetes. It can regulate human blood glucose level bi-directionally, by improving the balance in biochemical processes.

Examples

The method for preparing the Grain Worm dry powder includes the following steps:

A1. Wash and scour the collected whole Grain Worm to remove the dirt on the surface;

A2. Soak and disinfect the Grain Worm treated in Step A1, then rinse and drain;

A3. Put the drained Grain Worm into a freeze dryer (−20° C. to −50° C., equivalent to −4° F. to −58° F.) until it dries to a water content of less than 10% by weight (the yield is about 25%); It takes about 24 hours.

A4. The freeze-dried whole larvae are pulverized at low temperature to obtain the dried Grain Worm powder.

The method for preparing the Grain Worm tincture includes the following steps:

B1. Wash and scour the collected Grain Worm (Larvae) to remove the dirt on the surface;

B2. Soak and disinfect the Grain Worm treated in step B1, then rinse and drain;

B3. Store the drained whole Grain Worm into the liquor and seal it for at least 2 months;

B4. Take out the sealed Grain Worm and pulverize at low temperature to obtain the tincture.

In Steps A2 and B2, the disinfection solution used for the immersion disinfection is a mixture of water and peroxyacetic acid disinfection stock solution, and the soaking time is 10 minutes; The volume ratio of the water to peroxyacetic acid disinfection stock solution is 1:400.

In Step B3, the weight ratio of the whole Grain Worm to liquor is 1:4 to 2:3; The liquor is a pure grain liquor with an alcohol content of 55% to 70%.

The Grain Worm product can be in the form of capsule, tablet, pill, powder, compound granule, tincture, liquid agent, or a lyophilized powder.

The Grain Worm extract includes any water-soluble extract, chemical soluble extract from whole Grain Worm or Grain Worm dry powder, and/or their combinations.

For the patients with pre-diabetes, the recommended initial dosage is 1 g-1.5 g of Grain Worm powder before meal, 2-3 times a day, for a period of 1-2 cycles.

For the patients with mild diabetes, the recommended initial dosage is 1.5 g of Grain Worm powder before each meal, 3 times a day, plus 1 g-10 g of Grain Worm tincture before bedtime, for the first cycle. Starting on the second cycle, the dosage is 1.5 g of Grain Worm powder before each meal, 3 times a day only. A total of 4 cycles of treatment is recommended.

For the patients with moderate diabetes, the recommended initial dosage is 1.5 g of Grain Worm powder before each meal, 3 times a day, plus 1 g-10 g of Grain Worm tincture before bedtime, for the first cycle. Starting on the second cycle, take 1.5 g of Grain Worm powder before each meal, 3 times a day only. A total of 5 cycles of treatment is recommended.

For the patients with severe diabetes, the combined uses of Grain Worm dry powder, Grain Worm tincture, and the prescribed (western) medicine (only at the beginning of the first cycle for most cases) for 5-6 cycles are recommended.

Recommended dosage: For the $1^{st}$ cycle, take 1.5 g Grain Worm before each meal, three times a day. 1 g-10 g of Grain Worm tincture twice a day; one after breakfast and the other before bedtime. Combined with the regular (prescribed) western medicine(s). No exogenous insulin is needed during the treatment course. Monitor the glucose level daily. The regular prescribed (western) medicine(s) may be totally discontinued after blood glucose level is controlled. From the $2^{nd}$ to $6^{th}$ cycle, take 1.5 g of Grain Worm dry powder before each meal, 3 times a day. Based on patient's response to the treatment, 1 g-10 g of Grain Worm tincture may be taken before bedtime every day.

Examples of Medical Efficacy

The following are several T2DM patients treated using Grain Worm product. The diagnostic standards are from most recent World Health Organization (WHO) publications. Note that the blood glucose unit is mmol/L in this document. To convert the unit in mg/dL (commonly used in the US), multiply the value in mmol/L by 18.

The first example is for Patient J, a 34 year-old female. Prior to the Grain Worm treatment, the patient's OGTT data (Table 1) showed that she had hypoglycemia when fasting and hyperglycemia postprandially after 75 g glucose intake. The peak of blood glucose level was at two-hour time point. Because the patient was breast-feeding at that moment, the patient had not done the lifestyle change or taken any medication for glucose control. The treatment for Patient J is as follows: the patient took capsules containing 1.5 g of Grain Worm dry powder before meal, three times (i.e., 3×1.5 g) a day.

After 116 days of treatment, the Patient J took a second OGTT test (Table 1). The fasting blood glucose level changed from hypoglycemia (3.41 mmol/L or 61.38 mg/dl) to normal (4.88 mmol/L or 87.84 mg/dl). The two-hour blood glucose level decreased from 9.65 mmol/L (or 173.7 mg/dl) to 6.49 mmol/L (or 116.82 mg/dl). And the peak blood glucose level moved from 2-hour to 1-hour time point. The ratio of the area under the curve (AUC) for insulin to the AUC for glucose increased by 130%, indicating the improvement of β-cell function. Assessed using the WHO criteria, the patient has completely returned to normal.

TABLE 1

Comparison of OGTT results before and after treatment for Patient J

|  |  | Fasting | 30-Minute | 1-hour | 2-hour | 3-hour |
|---|---|---|---|---|---|---|
| Before | Plasma Glucose (mmol/L) | 3.41 | 6.62 | 8.84 | 9.65 | 7.14 |
|  | Plasma Insulin (mIU/L) | 0.7 | 11.2 | 15.3 | 15.0 | 12.2 |
| After | Plasma Glucose (mmol/L) | 4.88 | N/A | 9.14 | 6.49 | N/A |
|  | Plasma Insulin (mIU/L) | 3.2 | N/A | 30.8 | 32.1 | N/A |

The second example is for Patient Z, a 55 year-old male. The patient had a history of diabetes for 5 years before treatment. The OGTT data prior to Grain Worm treatment showed that the patient had fasting glucose level exceeded 7.0 mmol/L and 2-hour glucose level exceeded 11.1 mmol/L (Table 2). The treatment for Patient Z is as follows: Grain Worm capsules 3 times a day, a total of 4.5 g of Grain Worm dry powder daily, plus 15 ml of Grain Worm tincture before bedtime per day. The patient's blood glucose level was closely monitored every day. At the 19th day of the treatment, the patient stopped all western medicine.

Patient Z took another OGTT test (see Table 2) after 6 months of Grain Worm treatment (2 treatment cycles). Results showed that patient's fasting glucose level decreased from 8.41 to 5.41 mmol/L and 2-hour glucose level decreased from 17.92 to 10.71 mmol/L. Using HOMA-1[3] model, the patient's insulin resistance reduced by 73%. And the ratio of the AUC of insulin to the AUC of glucose increased by 5.3%, indicating the improvement of β-cell function.

TABLE 2

Comparison of OGTT results before and after treatment for Patient Z

|  |  | Fasting | 30-Minute | 1-hour | 2-hour | 3-hour |
|---|---|---|---|---|---|---|
| Before | Plasma Glucose (mmol/L) | 8.41 | N/A | 16.72 | 17.92 | 11.87 |
|  | Plasma Insulin (mIU/L) | 10.85 | N/A | 80.16 | 38.21 | 21.13 |
| After | Plasma Glucose (mmol/L) | 5.41 | 10.66 | 11.97 | 10.71 | 6.41 |
|  | Plasma Insulin (mIU/L) | 4.62 | 29.27 | 34.11 | 45.54 | 16.53 |

The third example is for Patient C, a 54 year-old female. Before the Grain Worm treatment, the patient had a history of diabetes for 16 years and relied on insulin injection (24 units per day) for controlling blood glucose level for about 14 years. The treatment for Patient C is as follows: Grain Worm capsules 3 times a day, a total of 4.5 g of Grain Worm dry powder daily, plus 10 ml of Grain Worm tincture before bedtime per day. There are no insulin injections for Patient C, who stopped all western medicine after Day 28 of the treatment.

After 2 treatment cycles (180 days), Patient C took another OGTT (Table 3). The insulin resistance[3] decreased by 46%. The ratio of the AUC of insulin to the AUC of glucose increased by 3.5%, indicating the improvement of β-cell function. Most importantly, the patient has no longer relied on insulin injection to achieve the blood glucose control.

TABLE 3

Comparison of OGTT results before and after treatment for Patient C

| OGTT |  | Fasting | 30-minute | 1-hour | 2-hour | 3-hour |
|---|---|---|---|---|---|---|
| Before (with Insulin injection) | Glucose (mmol/L) | 7.5 | N/A | 19.1 | 18.8 | 10.2 |
|  | Insulin (mIU/L) | 8.67 | N/A | 26.43 | 27.39 | 16.23 |
| After (without insulin injection) | Glucose (mmol/L) | 6.35 | 11.72 | 14 | 14.48 | 7.64 |
|  | Insulin (mIU/L) | 5.58 | 14.3 | 19.09 | 24.51 | 11.3 |

The fourth example is for Patient Y, a 58 year-old male. Prior to the Grain Worm treatment, the patient's blood glucose levels at both fasting and 2-hour were extremely high (Table 4). The treatment for Patient Y is as follows: Grain Worm capsules 3 times a day, a total of 4.5 g of Grain Worm dry powder daily, plus 15 ml of Grain Worm tincture before bedtime per day. Patient Y stopped all western medicine after Day 31 of the treatment.

At the 42nd day of treatment, i.e., 11 days after stopped all western medicine, Patient Y took another OGTT test (Table 4). The glucose tolerance was improved significantly. The insulin resistance[3] decreased by 34%. The ratio of the AUC of insulin to the AUC of glucose increased by 1,330%. The 30-minute insulinogenic index[4] increased by 2,888%. The oral disposition index[5] increased by 4,317%. All these indexes indicate the patient's β-cell function has been dramatically improved.

TABLE 4

Comparison of OGTT results before and after treatment for Patient Y

| | | Fasting | 30-Minute | 1-hour | 2-hour | 3-hour |
|---|---|---|---|---|---|---|
| Before | Plasma Glucose (mmol/L) | 3.41 | 6.62 | 8.84 | 9.65 | 7.14 |
| | Plasma Insulin (mIU/L) | 0.7 | 11.2 | 15.3 | 15.0 | 12.2 |
| After | Plasma Glucose (mmol/L) | 4.88 | N/A | 9.14 | 6.49 | N/A |
| | Plasma Insulin (mIU/L) | 3.2 | N/A | 30.8 | 32.1 | N/A |

What is claimed is:

1. A method of regulating blood glucose levels in an individual in need thereof, comprising:
   a) preparing a composition comprising Grain Worm comprising:
      i) a washing collected whole Grain Worm to remove dirt;
      ii) soaking and disinfecting the washed Grain Worm and subsequently rinsing and draining;
      iii) freeze-drying the drained Grain Worm until the water content thereof is less than 10% by weight; and
   b) administering to the individual an effective amount of the composition comprising Grain Worm, wherein the therapeutically effective amount of the Grain worm composition is administered for at least one or two cycles, each cycle continuing for about three months, wherein a daily dosage of the Grain worm is 2 g to 15 g.

2. The method as recited in claim 1 wherein said effective amount of said composition comprising Grain Worm treats diabetes.

3. The method as recited in claim 2 comprising conducting a treatment course to treat pre-diabetes comprising two cycles, wherein each cycle has a duration of approximately three months and comprises administering the composition comprising a total dosage of 2 g to 15 g of the Grain Worm per day during each of the two cycles.

4. The method as recited in claim 2 comprising conducting a treatment course to treat diabetes comprising at least four cycles, at least a first two of the at least four cycles comprising administering the composition comprising a total dosage of 3 g to 30 g of the Grain Worm per day and remaining ones of the at least four cycles comprising administering the composition comprising a total dosage of 3 g to 15 g of the Grain Worm per day.

5. The method as recited in claim 4 wherein each of the cycles has a duration of approximately three months.

6. The method as recited in claim 2 comprising conducting a treatment course to treat pre-diabetes comprising one cycle having a duration of approximately three months and comprising administering said composition comprising a total dosage of 2 g to 15 g of said Grain Worm per day during the one cycle.

7. The method as recited in claim 1 wherein the administering of the composition comprising Grain Worm comprises ingestion by the individual.

8. The method as recited in claim 1, further comprising forming a dry powder of the composition comprising Grain Worm by pulverizing freeze-dried whole larva of the Grain Worm at temperatures of −20 to −50° C.

9. The method as recited in claim 1, further comprising after step (a)(ii) storing the drained Grain Worm preparation in a liquor for at least two months and further comprising after step (a)(iii) pulverizing the preparation removed from the liquor at a temperature of −20 to −50° C.

10. The method as recited in claim 9 comprising preparing the liquor as grain liquor with an alcohol content of 55% to 70%.

11. The method as recited in claim 1, wherein said composition comprising said Grain Worm is administered at least two times per day.

12. The method as recited in claim 1 comprising conducting a treatment course of at least four cycles, wherein each cycle has a duration of approximately three months and comprises administering said composition comprising Grain Worm at least once per day during each of said cycles.

13. The method as recited in claim 12 comprising conducting a treatment course to treat diabetes comprising six cycles, at least a first two of said six cycles comprising administering said composition comprising a total dosage of 3 g to 30 g of said Grain Worm per day and remaining ones of said six cycles comprising administering said composition comprising a total of 3 g to 15 g of said Grain Worm per day.

14. The method as recited in claim 1 further comprising conducting a treatment course of no more than six cycles wherein each cycle has a duration of approximately three months and comprises administering said composition comprising Grain worm at least once per day during each of said cycles.

15. A method of regulating blood glucose levels in an individual in need thereof, comprising:
   administering to the individual an effective amount of a composition comprising Grain Worm wherein said effective amount of said composition comprising Grain Worm treats diabetes, and
   conducting a treatment course to treat pre-diabetes comprising two cycles, wherein each cycle has a duration of approximately three months and comprises administering the composition comprising a total dosage of 2 g to 15 g of the Grain Worm per day during each of the two cycles.

16. A method of regulating blood glucose levels in an individual in need thereof, comprising:
   a) preparing a composition comprising Grain Worm comprising:
      i) washing collected whole Grain Worm to remove dirt;
      ii) soaking and disinfecting the washed Grain Worm and subsequently rinsing and draining;
      iii) freeze-drying the drained Grain Worm until the water content thereof is less than 10% by weight; and
   b) administering to the individual an effective amount of the composition comprising Grain Worm, wherein the therapeutically effective amount of the Grain worm composition is administered for at least one cycle, wherein the cycle continues for about three months, wherein a daily dosage of the Grain worm is 2 g to 30 g.

* * * * *